(12) United States Patent
Spargo et al.

(10) Patent No.: US 12,168,011 B2
(45) Date of Patent: Dec. 17, 2024

(54) FORMULATION PRODUCTION PROCESS

(71) Applicant: Verona Pharma PLC, Cardiff (GB)

(72) Inventors: Peter Lionel Spargo, Canterbury (GB); Phillip A. Haywood, Buntingford (GB); Edward James French, Canterbury (GB)

(73) Assignee: Verona Pharma PLC, Cardiff (GB)

( * ) Notice: Subject to any disclaimer, the term of this patent is extended or adjusted under 35 U.S.C. 154(b) by 0 days.

(21) Appl. No.: 18/422,922

(22) Filed: Jan. 25, 2024

(65) Prior Publication Data

US 2024/0165117 A1    May 23, 2024

Related U.S. Application Data

(63) Continuation of application No. PCT/GB2023/050372, filed on Feb. 20, 2023.

(30) Foreign Application Priority Data

Feb. 21, 2022    (GB) ..................................... 2202297

(51) Int. Cl.
A61K 31/519    (2006.01)
A61K 9/00    (2006.01)
A61K 9/16    (2006.01)

(52) U.S. Cl.
CPC .......... *A61K 31/519* (2013.01); *A61K 9/0075* (2013.01); *A61K 9/1682* (2013.01)

(58) Field of Classification Search
CPC ................................ A61K 31/513; A61L 2/00
See application file for complete search history.

(56) References Cited

U.S. PATENT DOCUMENTS

| | | |
|---|---|---|
| 4,482,556 A | 11/1984 | Lal et al. |
| 5,378,818 A | 1/1995 | Mayer et al. |
| 5,985,878 A | 11/1999 | Stokbroekx et al. |
| 6,794,391 B2 | 9/2004 | Oxford et al. |
| 7,105,663 B2 | 9/2006 | Oxford et al. |
| 7,378,424 B2 | 5/2008 | Oxford et al. |
| 8,221,772 B2 | 7/2012 | Johnson et al. |
| 8,242,127 B2 | 8/2012 | Oxford et al. |
| 9,062,047 B2 | 6/2015 | Walker et al. |
| 9,700,558 B2 | 7/2017 | Walker et al. |
| 9,717,732 B2 | 8/2017 | Walker et al. |
| 9,956,171 B2 | 5/2018 | Spargo et al. |
| 10,463,665 B2 | 11/2019 | Spargo et al. |
| 10,471,063 B2 | 11/2019 | Walker et al. |
| 10,710,998 B2 | 7/2020 | Spargo |
| 10,864,213 B2 | 12/2020 | Abbott-Banner et al. |
| 10,945,950 B2 | 3/2021 | Spargo et al. |
| 11,491,155 B2 | 11/2022 | Spargo et al. |
| 11,759,467 B2 | 9/2023 | Abbott-Banner et al. |
| 2003/0036542 A1 | 2/2003 | Oxford et al. |
| 2003/0229108 A1 | 12/2003 | De Belin et al. |
| 2004/0076668 A1 | 4/2004 | Berchielli et al. |
| 2004/0171828 A1 | 9/2004 | Oxford et al. |
| 2004/0176353 A1 | 9/2004 | Oxford et al. |
| 2004/0247628 A1 | 12/2004 | Lintz et al. |
| 2005/0054655 A1 | 3/2005 | Beaulieu et al. |
| 2005/0186276 A1 | 8/2005 | Berchielli et al. |
| 2005/0261271 A1 | 11/2005 | Feng et al. |
| 2007/0197489 A1* | 8/2007 | Karlsson ................. A61P 11/06 514/174 |
| 2008/0003283 A1 | 1/2008 | Feng et al. |
| 2008/0108807 A1 | 5/2008 | Feng et al. |
| 2008/0108808 A1 | 5/2008 | Feng et al. |
| 2008/0113993 A1 | 5/2008 | De Belin et al. |
| 2008/0125437 A1 | 5/2008 | Dong et al. |
| 2008/0142759 A1 | 6/2008 | Pays |
| 2008/0161562 A1 | 7/2008 | Feng et al. |
| 2008/0177064 A1 | 7/2008 | Feng et al. |
| 2008/0188501 A1 | 8/2008 | Feng et al. |
| 2008/0199410 A1 | 8/2008 | Johnson et al. |
| 2008/0206163 A1 | 8/2008 | Oxford et al. |
| 2009/0012059 A1 | 1/2009 | Feng et al. |
| 2009/0075939 A1 | 3/2009 | He et al. |
| 2010/0113413 A1 | 5/2010 | Dong et al. |
| 2010/0204471 A1 | 8/2010 | Dong et al. |

(Continued)

FOREIGN PATENT DOCUMENTS

| | | |
|---|---|---|
| AU | 527997 B2 | 3/1983 |
| DE | 2847693 A1 | 5/1980 |

(Continued)

OTHER PUBLICATIONS

SPAN 20 (sorbitan monolaurate product page) (Year: 2024).*
TWEEN 20 (polyoxyethylene sorbitan monolaurate product page) (Year: 2024).*
Akers (Sterile Drug Products: Formulation, Packaging, Manufacture and Quality. Published 2010) (Year: 2010).*
Bjermer, L. et al., Efficacy and safety of a first-in-class inhaled PDE3/4 inhibitor (ensifentrine) vs salbutamol in asthma, Pulmonary Pharmacology & Therapeutics, vol. 58, (2019).
Blasko, G. et al., Pyrimido[1,6-a]pyrido[3,4-b]indoles as new platelet inhibiting agents, European Journal of Medicinal Chemistry, vol. 21, 2 (1986):91-5.
Chen, E.H. et al., Modifications of primaquine as antimalarials. 1. 5-Phenoxy derivatives of primaquine, Journal of Medicinal Chemistry, vol. 20, 8 (1977):1107-9.
Dong-Sheng, M. et al., Synthesis of Daimuron, College of Chemistry and Chemical Engineering, Huaxue Yu Nianhe, vol. 6, (2003):293-295.

(Continued)

*Primary Examiner* — Clinton A Brooks
*Assistant Examiner* — George W Kosturko
(74) *Attorney, Agent, or Firm* — Foley & Lardner LLP

(57) ABSTRACT

The present invention relates to a process for producing a sterile liquid pharmaceutical composition suitable for administration by inhalation comprising ensifentrine particles, wherein the process comprises: (a) heating ensifentrine particles at a temperature of from 100° C. to 220° C. to obtain sterile ensifentrine particles; and (b) combining the sterile ensifentrine particles with a sterile liquid vehicle to produce the sterile liquid pharmaceutical composition suitable for administration by inhalation. A process for producing an ampule comprising the sterile liquid pharmaceutical composition is also described.

25 Claims, No Drawings

(56) References Cited

U.S. PATENT DOCUMENTS

| | | |
|---|---|---|
| 2011/0076276 A1 | 3/2011 | Guo et al. |
| 2011/0190261 A1 | 8/2011 | Dong et al. |
| 2012/0251594 A1 | 10/2012 | Longest et al. |
| 2012/0302533 A1 | 11/2012 | Oxford et al. |
| 2013/0078256 A1 | 3/2013 | Guo et al. |
| 2013/0158021 A1 | 6/2013 | Dong et al. |
| 2013/0225616 A1 | 8/2013 | Walker et al. |
| 2016/0000790 A1 | 1/2016 | Walker et al. |
| 2016/0008363 A1 | 1/2016 | Walker et al. |
| 2017/0112839 A1 | 4/2017 | Abbott-Banner et al. |
| 2017/0239178 A1 | 8/2017 | Spargo et al. |
| 2017/0266190 A1 | 9/2017 | Walker et al. |
| 2018/0021337 A1 | 1/2018 | Spargo et al. |
| 2018/0369139 A1 | 12/2018 | Spargo et al. |
| 2019/0330206 A1 | 10/2019 | Spargo |
| 2020/0016158 A1 | 1/2020 | Spargo et al. |
| 2021/0106585 A1 | 4/2021 | Abbott-Banner et al. |
| 2021/0379053 A1 | 12/2021 | Spargo et al. |
| 2022/0265549 A1 | 8/2022 | Spargo et al. |
| 2023/0112220 A1 | 4/2023 | Spargo et al. |

FOREIGN PATENT DOCUMENTS

| | | | |
|---|---|---|---|
| DE | 4240981 A1 | 6/1994 | |
| DE | 19612194 A1 | 10/1997 | |
| DE | 19820947 A1 | 11/1998 | |
| DE | 19821263 A1 | 11/1998 | |
| DE | 19726241 A1 | 12/1998 | |
| EP | 0601401 A1 | 6/1994 | |
| EP | 0876366 A2 | 11/1998 | |
| EP | 0983334 A1 | 3/2000 | |
| EP | 1305026 A2 | 5/2003 | |
| EP | 1418896 A2 | 5/2004 | |
| EP | 1438019 A1 | 7/2004 | |
| EP | 1519711 A1 | 4/2005 | |
| EP | 1586571 A1 | 10/2005 | |
| EP | 1651611 A2 | 5/2006 | |
| EP | 1825467 A2 | 8/2007 | |
| EP | 1892269 A1 | 2/2008 | |
| EP | 1993540 A2 | 11/2008 | |
| EP | 2063903 A1 | 6/2009 | |
| EP | 2167476 A2 | 3/2010 | |
| JP | 2001213867 A | 8/2001 | |
| JP | 3675274 B2 | 7/2005 | |
| JP | 2005263780 A | 9/2005 | |
| KR | 101361145 B1 | 2/2014 | |
| WO | WO-9726258 A1 | 7/1997 | |
| WO | WO-9736039 A1 | 10/1997 | |
| WO | WO-9845293 A1 | 10/1998 | |
| WO | WO-9851772 A1 | 11/1998 | |
| WO | WO-9901607 A1 | 1/1999 | |
| WO | WO-0058308 A1 | 10/2000 | |
| WO | WO-0058309 A1 | 10/2000 | |
| WO | WO-0193841 A2 | 12/2001 | |
| WO | WO-03000343 A2 | 1/2003 | |
| WO | WO-03035030 A1 | 5/2003 | |
| WO | WO-03037262 A2 | 5/2003 | |
| WO | WO-2004004684 A1 | 1/2004 | |
| WO | WO-2005007092 A2 | 1/2005 | |
| WO | WO-2005007138 A1 | 1/2005 | |
| WO | WO-2005021510 A2 | 3/2005 | |
| WO | WO-2005095381 A1 | 10/2005 | |
| WO | WO-2006061398 A2 | 6/2006 | |
| WO | WO-2008023249 A1 | 2/2008 | |
| WO | WO-2008036293 A1 | 3/2008 | |
| WO | WO-2008140553 A2 | 11/2008 | |
| WO | WO-2009005674 A2 | 1/2009 | |
| WO | WO-2012020016 A1 * | 2/2012 | ........... A61K 31/519 |
| WO | WO-2012037782 A1 | 3/2012 | |
| WO | WO-2012051426 A2 | 4/2012 | |
| WO | WO-2013063468 A1 | 5/2013 | |
| WO | WO-2013092791 A1 | 6/2013 | |
| WO | WO-2013118855 A1 | 8/2013 | |
| WO | WO-2013128283 A2 | 9/2013 | |
| WO | WO-2014140647 A1 * | 9/2014 | ........... A61K 31/137 |
| WO | WO-2014140648 A1 | 9/2014 | |
| WO | WO-2015173551 A1 | 11/2015 | |
| WO | WO-2016042313 A1 * | 3/2016 | ........... A61K 31/495 |
| WO | WO-2016128742 A1 | 8/2016 | |
| WO | WO-2018020249 A1 | 2/2018 | |
| WO | WO-2020074894 A1 | 4/2020 | |
| WO | WO-2021028679 A1 | 2/2021 | |
| WO | WO-2021171034 A1 | 9/2021 | |

OTHER PUBLICATIONS

Franciosi, L.G. et al., Efficacy and safety of RPL554, a dual PDE3 and PDE4 inhibitor, in healthy volunteers and in patients with asthma or chronic obstructive pulmonary disease: findings from four clinical trials, The Lancet. Respiratory Medicine, vol. 1, 9(2013):714-727.

Frank, A.W., Synthesis of some carbonyl derivatives of tris(aminomethyl)phosphine oxide, Phosphorus and Sulfur and the Related Elements, vol. 22, 3(1985):265-76.

Houlihan, W.J. et al., Synthesis and proton-NMR spectra, Journal of Heterocyclic Chemistry, vol. 19, 6(1982):1453-6.

Jansen, M., Derivatives of some nuclear methoxylated B-phenylethylamines, vol. 50, (1931):617-37.

Kienzle, F. et al., Synthesis of 6,7-dihydro-2H-pyrimido[6,1-a]isoquinolin-4(3H)-ones and analogous compounds and their activity as blood platelet aggregation inhibitors, Helvetica Chimica Acta, vol. 69, 7(1986): 1671-80.

Kijima, I, et al., Synthesis and reactivities of triisocyanatoantimony, Japan, Nippon Kagaku Kaishi, vol. 12, (1986):1754-57.

Lai, B. et al., Synthesis of 2-substituted-6,7-dihydro-4H-pyrimido[6,1-a]thieno[2,3-c]- and [3,2-c]pyridin-4-ones, Heterocycles, vol. 24, 7(1986):1977-85.

Lal, B. et al., Trequinsin, a potent new antihypertensive vasodilator in the series of 2-(arylimino)-3-alkyl-9,10-dimethoxy-3,4,6,7-tetrahydro-2H-pyrimido[6,1-a]isoquinolin-4-ones, Journal of Medicinal Chemistry, vol. 27, 11(1984):1470-80.

Mannich, C. et al., Berichte der Deutschen Chemischen Gesellschaft, vol. 43, (1910):189-97.

No Author, European Medicines Agency, Guideline on the sterilisation of the medicinal product, active substance, excipient and primary container, Apr. 11, 2016.

No Author, European Medicines Agency, Guideline on the sterilisation of the medicinal product, active substance, excipient and primary container, Mar. 6, 2019.

Pai, N.R. et al., Synthesis of novel analogs 3,4-dihydro-1H-quinolin-2-one derivatives as typical Antidepressant, Sedative and anti-Parkinson agents, Heterocyclic Letters, vol. 2, 1 (2012):117-128.

Pfleiderer, V.W. et al., Synthesis of 9-substituted xanthines, Justus Liebigs Annalen der Chemie, vol. 631, (1960):168-74.

Ratel, M. et al., Imidazolium-Based Ionic Liquid Surfaces for Biosensing, Analytical Chemistry, vol. 85, 12 (2013):5770-5777.

Tran, P. et al., Structure-activity relationship of human glutaminyl cyclase inhibitors having an N-(5-methy-1H-imidazol-1-yl)propyl thiourea template, Bioorganic & Medicinal Chemistry, vol. 21, 13 (2013):3821-3830.

USP 1229.8 Dry Heat Sterilization 2018.

* cited by examiner

FORMULATION PRODUCTION PROCESS

CROSS REFERENCE

This application is a continuation of International Patent Application No. PCT/GB2023/050372, filed Feb. 20, 2023, which claims the benefit of GB Application No. 2202297.4, filed Feb. 21, 2022, each of which is incorporated herein by reference in their entirety.

FIELD OF THE INVENTION

The present invention relates to a process for producing a sterile formulation comprising an active pharmaceutical ingredient.

BACKGROUND OF THE INVENTION

Certain pharmaceutical products must meet stringent sterility standards before they can be administered to patients. In view of the importance of sterility for pharmaceutical products, a large number of different processes, protocols and techniques have been developed for sterilisation of pharmaceutical products. These include steam sterilisation, dry heat sterilisation, ionising radiation sterilisation (including x-ray and gamma-ray sterilisation), gas sterilisation, sterile filtration and aseptic processing. The selection of a sterilisation protocol for a new pharmaceutical product is a complex process which relies on evaluation of the various available methods and their suitability for the specific product.

Ensifentrine (N-(2-{(2E)-9,10-dimethoxy-4-oxo-2-[(2,4,6-trimethylphenyl)imino]-6,7-dihydro-2H-pyrimido[6,1-a]isoquinolin-3(4H)-yl}ethyl)urea; also known as RPL554) is a dual PDE3/PDE4 inhibitor and is described in WO 00/58308 A1. Ensifentrine has both bronchodilatory and anti-inflammatory activity and is useful in the treatment of respiratory disorders such as asthma and chronic obstructive pulmonary disease (COPD). The structure of ensifentrine is shown below.

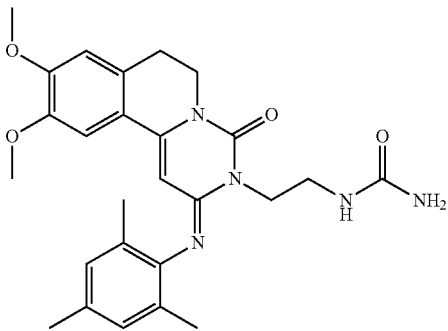 [SMILES: COc1cc2c(cc1OC)-c1c/c(=N\c3c(C)cc(C)cc3C)n(CCNC(N)=O)c(=O)n1CC2]

Ensifentrine may be formulated as a suspension of particles in a diluent as described in WO 2016/042313 A1.

No suitable method for sterilising a liquid pharmaceutical composition comprising ensifentrine particles has been described. There is a need to develop a process for producing a sterilised ensifentrine suspension.

SUMMARY OF THE INVENTION

The inventors have found that, of all the available sterilisation techniques, dry heat sterilization of particles of active agent followed by aseptic compounding is particularly well-suited to formulation of ensifentrine as a suspension. Other techniques such as terminal sterilisation or dry gamma-ray sterilisation were found to cause degradation of the formulations.

The invention accordingly provides a process for producing a sterile liquid pharmaceutical composition suitable for administration by inhalation comprising ensifentrine particles, wherein the process comprises: (a) heating ensifentrine particles at a temperature of from 100° C. to 220° C. to obtain sterile ensifentrine particles, and (b) combining the sterile ensifentrine particles with a sterile liquid vehicle to produce the sterile liquid pharmaceutical composition suitable for administration by inhalation.

The invention further provides a process for producing an ampule comprising a sterile liquid pharmaceutical composition suitable for administration by inhalation, the process comprising: (i) producing a sterile liquid pharmaceutical composition suitable for administration by inhalation comprising ensifentrine particles by the process defined herein, and (ii) filling an ampule with the sterile liquid pharmaceutical composition suitable for administration by inhalation.

DETAILED DESCRIPTION OF THE INVENTION

The process of the invention produces a sterile liquid pharmaceutical composition. The sterile liquid pharmaceutical composition is suitable for administration by inhalation. The sterile liquid pharmaceutical composition comprises sterile ensifentrine particles.

The term "sterile" refers to a composition which is essentially free of viable microbes. As such, a sterile composition is typically a composition which is substantially free of viable bacteria or fungi. The term "sterile" is well known in the art.

The sterile liquid pharmaceutical composition may have a sterility assurance level (SAL) of less than or equal to $10^{-3}$, less than or equal to $10^{-6}$, or less than or equal to $10^{-9}$. For instance, an SAL of $10^{-6}$ means that the probability that a final product is non-sterile is $1/10^6$. The sterile liquid pharmaceutical composition may have a total bioburden limit of less than or equal to 10 CFU/mL, or less than or equal to 1 CFU/mL. "CFU" is a colony forming unit. The bioburden may be as measured using a plate count method as described in USP 31<61>, for instance the pour-plate method.

Typically, the sterility of the liquid pharmaceutical composition is as determined in accordance with USP<71> or Ph Eur 2.6.1. The liquid pharmaceutical composition typically meets the acceptance criteria as defined in USP<71> or Ph Eur2.6.1.

The pharmaceutical composition is a liquid pharmaceutical composition and, as such, is liquid under ambient conditions (for instance at temperatures from 10 to 40° C.).

The sterile liquid pharmaceutical composition comprises sterile ensifentrine particles. The ensifentrine particles comprise ensifentrine (i.e. ensifentrine free base) or a pharmaceutically acceptable salt thereof. Typically, the ensifentrine particles comprise ensifentrine free base. The ensifentrine particles typically comprise at least 90.0 wt % of ensifentrine or a pharmaceutically acceptable salt thereof, preferably at least 95.0 wt %. The ensifentrine particles may consist essentially of ensifentrine or a pharmaceutically acceptable salt thereof, or may consist of ensifentrine or a pharmaceutically acceptable salt thereof. For instance, the ensifentrine particles may consist of ensifentrine free base.

A composition which consists essentially of a component comprises only that component and other components which do not materially affect the essential characteristics of the component of which the composition essentially consists. A composition consisting essentially of a component typically comprises at least 99.5 wt % of that component relative to the total weight of the composition.

The sterile ensifentrine particles in the sterile liquid pharmaceutical composition may be suspended in the sterile liquid vehicle. The sterile liquid pharmaceutical composition accordingly typically comprises a suspension of the ensifentrine particles. It may also be the case that some or all of the ensifentrine particles in the sterile liquid pharmaceutical composition have settled to the bottom of a receptacle containing the sterile liquid pharmaceutical composition, for instance after storage for a period of time. The ensifentrine particles may be re-suspended in any suitable way, for instance by agitation of the sterile liquid pharmaceutical composition.

Step (a) of the process typically comprises heating the ensifentrine particles at a temperature of from 120° C. to 200° C. The process may comprise heating the ensifentrine particles at a temperature of from 140° C. to 180° C., for instance from 150° C. to 170° C. or from 155° C. to 165° C.

The ensifentrine particles may be heated for any period of time suitable for producing sterile ensifentrine particles. The process typically comprises heating the ensifentrine particles at the temperature for a time of from 10 minutes to 24 hours. The process may comprise heating the ensifentrine particles at the temperature for a time of from 30 minutes to 360 minutes, for instance from 45 minutes to 160 minutes or from 60 minutes to 140 minutes.

The process preferably comprises heating the ensifentrine particles at a temperature of from 145° C. to 175° C. for a time of from 45 minutes to 160 minutes. For instance, the process may comprise heating the ensifentrine particles at a temperature of from 155° C. to 165° C. for a time of from 110 minutes to 130 minutes.

Heating the ensifentrine particles at a temperature in a certain range for a certain time means that the temperature of the ensifentrine particles is held at a temperature within that range for the total time. The ensifentrine particles are typically heated for the relevant time in a single heating step, but the heating may alternatively be conducted in two or more separate heating steps. For instance, heating at a temperature of from 140° C. to 180° C. for 60 minutes may comprising a single heating step for a duration of 60 minutes or two separate heating steps each having a duration of 30 minutes. Typically the ensifentrine particles are heated in a single heating step at the temperature for the time.

Step (a) is typically a dry heat sterilisation process. The ensifentrine particles are typically in the form of a dry powder. The process accordingly may comprise heating a dry powder comprising ensifentrine particles at a temperature of from 100° C. to 220° C. to obtain a sterile dry powder comprising ensifentrine particles. Typically, the ensifentrine particles are subjected to dry-heat treatment on their own. The process may comprise heating a dry powder of ensifentrine particles (i.e. a dry powder consisting essentially of ensifentrine particles) at a temperature of from 100° C. to 220° C. to obtain a sterile dry powder of ensifentrine particles. A dry powder is typically a powder having a water content of less than 5.0 wt %, less than 1.0 wt % or less than 0.1 wt %.

The ensifentrine particles typically have a particle size distribution with a Dv50 of from 0.5 µm to 5.0 µm. The ensifentrine particles preferably have a Dv50 of from 1.0 µm to 2.0 µm. Typically, the Dv10 of the ensifentrine particles is from 0.2 µm to 1.0 µm and the Dv90 of the ensifentrine particles is from 2.5 µm to 6.0 µm. For instance, the Dv10 of the ensifentrine particles may be from 0.4 µm to 0.6 µm and the Dv90 of the ensifentrine particles may be from 2.8 µm to 4.2 µm.

Particle sizes are described herein by reference to the Dv50 value, which is the median particle size for a volume distribution. Thus, half the volume of the particles have diameters of less than the Dv50 value and half the volume of the particles have diameters of greater than the Dv50 value. This is a well-known manner in which to describe particle size distributions. The parameters of Dv10 and Dv90 may also be used to characterise a particle size distribution of a sample. 10% of the volume of particles have a diameter of less than the Dv10 value. 90% of the volume of the particles have a diameter of less than the Dv90 value.

The technique used to measure the Dv50 (and Dv10 and Dv90) values as stated herein is typically laser diffraction. The particle size distribution of the ensifentrine particles may be as measured by laser diffraction using a wet powder dispersion system. For instance, the particle size distribution can be measured by laser diffraction using a Malvern Spraytec in conjunction with a wet dispersion cell.

Typically, the instrument parameters for the Malvern Spraytec are as follows:
particle—standard opaque particle;
refractive index Particle—1.50;
refractive index (imaginary)—0.50;
density of particle—1.00;
refractive index of dispersant—1.33;
controller unit—1000 RPM;
measurement type—timed;
initial sampling time—30 s;
obscuration—20%-30%;
dispersant—1% Polysorbate 20 in deionised water.

The ensifentrine particles may be produced by any pharmaceutically acceptable size reduction process or particle size controlled production process. For instance, the particles may be produced by spray-drying a solution of ensifentrine, by controlled crystallisation, or by size reduction of a solid form of ensifentrine, for example by air jet milling, mechanical micronisation or media milling.

The process further comprises combining the sterile ensifentrine particles with a sterile liquid vehicle to produce the sterile liquid pharmaceutical composition suitable for administration by inhalation. Combining the sterile ensifentrine particles with a sterile liquid vehicle typically comprises mixing the sterile ensifentrine particles with a sterile liquid vehicle.

The sterile liquid vehicle typically comprises one or more diluents. The diluent may be any suitable liquid diluent. For instance, the sterile liquid vehicle typically comprises a diluent which is water. The sterile liquid vehicle may comprise one or more additional diluents or the sterile liquid vehicle may comprise a single diluent. The sterile liquid vehicle may comprise a single diluent which is water.

A sterile liquid vehicle comprising water may be used to produce a sterile liquid pharmaceutical composition suitable for use in a nebulizer. The sterile liquid vehicle typically further comprises one or more additional excipients selected from surfactants, buffers and tonicity adjusters.

The sterile liquid vehicle typically further comprises a tonicity adjuster. Examples of tonicity adjusters include sodium chloride, potassium chloride, glucose, glycerine and mannitol. Preferably, the tonicity adjuster is sodium chloride.

The concentration of the tonicity adjuster in the sterile liquid vehicle is typically greater than or equal to 1.0 mg/mL (for instance from 1.0 to 50.0 mg/mL). Preferably, the tonicity adjuster concentration is from 4.0 to 20.0 mg/mL or from 6.0 to 12.0 mg/mL.

The sterile liquid vehicle typically further comprises one or more surfactants. The one or more surfactant may comprise a non-ionic surfactant, an anionic surfactant, a cationic surfactant, a zwitterionic surfactant or a mixture thereof. Typically, the one or more surfactants comprise a non-ionic surfactant.

Examples of surfactants include lecithin, oleic acid, polyoxyethylene glycol alkyl ethers (for instance PEG 300, PEG 600, PEG 1000, Brij 30, Brij 35, Brij 56, Brij 76 and Brij 97), polypropylene glycol (for instance PPG 2000), glucoside alkyl ethers, polyoxyethylene glycol octylphenol ethers, polyoxyethylene glycol alkylphenol ethers, glycerol alkyl esters, polyoxyethylene glycol sorbitan alkyl esters (polysorbates, for instance polysorbate 20, polysorbate 40, polysorbate 60 and polysorbate 80), sorbitan alkyl esters (for instance sorbitan monolaurate (Span® 20), sorbitan monooleate (Span® 80) and sorbitan trioleate (Span® 85)), cocamide MEA, cocamide DEA, dodecyldimethylamine oxide, block copolymers of polyethylene glycol and polypropylene glycol (poloxamers), block copolymers of polyethylene glycol and polypropylene oxide (for instance Pluronic surfactants), polyvinyl pyrrolidone K25, polyvinyl alcohol, oligolactic acid, sodium dioctyl sulfosuccinate and polyethoxylated tallow amine (POEA).

Preferably, the one or more surfactants comprise a polysorbate and/or a sorbitan alkyl ester. The one or more surfactants may for instance comprise polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate) or polysorbate 80 (polyoxyethylene (20) sorbitan monooleate). The one or more surfactants may for instance comprise sorbitan monolaurate (Span® 20), sorbitan monooleate (Span® 80) or sorbitan trioleate (Span® 85). Preferably, the sterile liquid vehicle comprises polysorbate 20 and/or sorbitan monolaurate (Span® 20).

The sterile liquid vehicle may comprise two or more surfactants, or the sterile liquid vehicle may comprise a single surfactant. For instance the composition may comprise a single surfactant which is a polysorbate, for instance polysorbate 20. The sterile liquid vehicle may comprise two or more surfactants. For instance, the sterile liquid vehicle may comprise polysorbate 20 and sorbitan monolaurate (Span® 20).

The total concentration of the one or more surfactants in the sterile liquid vehicle is typically from 0.01 to 2.0 mg/mL. Preferably, the total surfactant concentration is from 0.1 to 1.0 mg/mL. For instance, the total surfactant concentration in the sterile liquid vehicle may be from 0.25 to 0.75 mg/mL. The sterile liquid vehicle may for instance comprise a polysorbate at a concentration of from 0.1 to 1.0 mg/mL and optionally a sorbitan alkyl ester at a concentration of from 0.01 to 0.1 mg/mL.

The sterile liquid vehicle typically further comprises one or more buffers. The buffer can be used to control the pH of the liquid pharmaceutical composition. A buffer typically comprises a weak acid and its conjugate base. Examples of buffers include a citrate buffer, a phosphate buffer, an acetate buffer, and a bicarbonate buffer.

Preferably, the buffer is a phosphate buffer. For instance, the sterile liquid vehicle may comprise sodium dihydrogen phosphate dihydrate and/or disodium phosphate dihydrate.

The pH of the sterile liquid vehicle is typically from 6.0 to 7.5, for instance from 6.2 to 7.2. The pH of the sterile liquid vehicle may be from 6.5 to 6.9. The pH of the sterile liquid vehicle is typically the pH as measured at a temperature of 20° C. The pH of the sterile liquid vehicle may be measured by any suitable technique. For instance, the pH may be as measured using a potentiometric pH meter.

The total concentration of the one or more buffers in the sterile liquid vehicle is typically from 0.1 to 20.0 mg/mL. Preferably the buffer concentration is from 1.0 to 2.0 mg/mL. The concentration of the buffer includes both the acid and conjugate base components of the buffer.

Typically, the sterile liquid vehicle comprises: water, one or more tonicity adjusters, one or more buffers, and one or more surfactants. The sterile liquid vehicle may for instance comprise: water, sodium chloride, sodium dihydrogen phosphate dihydrate, disodium phosphate dihydrate, polysorbate 20 and sorbitan laurate.

The process typically further comprises producing the sterile liquid vehicle. The sterile liquid vehicle may be produced by sterilising a liquid vehicle, for instance by aseptic filtration, heat treatment or gamma-ray treatment of a liquid vehicle. The sterile liquid vehicle is typically produced by aseptic filtration of a liquid vehicle. Aseptic filtration typically comprises filtering a liquid vehicle through a filter having a nominal pore size of no greater than 0.5 µm, or no greater than 0.3 µm (for instance around 0.2 µm).

The process of the invention produces a sterile liquid pharmaceutical composition through aseptic processing and compounding. As such, the process typically does not further comprise an additional step of terminal sterilisation (which has been found to cause the presence of impurities in the composition). For instance, the process typically does not further comprise heating the sterile liquid pharmaceutical composition suitable for administration by inhalation comprising ensifentrine particles at a temperature of 100° C. or greater.

The concentration of ensifentrine particles in the sterile liquid pharmaceutical composition produced by the process can be any suitable concentration, for instance from 0.01 to 400 mg/mL. Typically, the concentration of ensifentrine particles is from 0.1 to 5.0 mg/mL. Preferably, the concentration of ensifentrine particles is from 0.1 to 2.5 mg/mL. For instance, the concentration of ensifentrine particles may be from 0.15 to 0.5 mg/mL or from 1.0 to 2.0 mg/mL.

For instance, the sterile liquid pharmaceutical composition may comprise:
water;
particles consisting of ensifentrine free base at a concentration of from 0.1 to 20 mg/mL;
one or more tonicity adjusters at a total concentration of from 1.0 to 15 mg/mL;
one or more buffers at a total concentration of from 0.1 to 4 mg/mL; and
one or more surfactants at a total concentration of from 0.05 to 3 mg/mL.

The sterile liquid pharmaceutical composition may comprise:
water;
particles consisting of ensifentrine free base at a concentration of from 0.5 to 6 mg/mL;
sodium chloride at a concentration of from 5 to 12 mg/mL;
sodium dihydrogen phosphate dihydrate at a concentration of from 0.3 to 2 mg/mL;

disodium phosphate dihydrate at a concentration of from 0.3 to 2 mg/mL;

polysorbate 20 at a concentration of from 0.1 to 1.5 mg/mL; and sorbitan laurate at a concentration of from 0.01 to 0.5 mg/mL.

The invention also provides a process for producing an ampule comprising a sterile liquid pharmaceutical composition suitable for administration by inhalation. The process comprises: (i) producing a sterile liquid pharmaceutical composition suitable for administration by inhalation comprising ensifentrine particles by a process as defined herein; and (ii) filling an ampule with the sterile liquid pharmaceutical composition suitable for administration by inhalation. The ampule may be a glass ampule or a plastic ampule. The ampule is typically a polyethylene plastic ampule. The ampule may be individually overwrapped in an aluminium foil pouch after filling.

The ampule may be a blow-fill-seal ampule. For instance, the process may be a process for producing an ampule using blow-fill-seal technology, which ampule comprises a sterile liquid pharmaceutical composition suitable for administration by inhalation, the process comprising: (i) producing a sterile liquid pharmaceutical composition suitable for administration by inhalation comprising ensifentrine particles by the process defined herein; and (ii) producing a blow-fill-seal ampule filled with the sterile liquid pharmaceutical composition suitable for administration by inhalation.

EXAMPLES

Methods

Assay testing was performed in duplicate with the key high performance liquid chromatography (HPLC) parameters shown in Table 1.

TABLE 1

| Assay parameters | |
|---|---|
| Mobile phase | Acetonitrile:water:TFA 45:55:0.1 |
| Column | Waters X-Bridge phenyl, 3.5 µm, 150 × 4.6 mm |
| Column temperature | 40° C. |
| Flow rate | 1.5 mL/min |
| Injection volume | 10 µL |
| Detection | UV@ 254 nm |
| Runtime | 6 minutes |
| Autosampler temperature | Ambient |
| Sample and standard concentration | 0.1 mg/mL |

Impurities determination was performed in duplicate with the key high performance liquid chromatography (HPLC) parameters shown in Table 2.

TABLE 2

| Impurities determination parameters | |
|---|---|
| Mobile phase | A - Purified water/Acetonitrile/TFA (95/5/0.1) |
| | B - Acetonitrile/Water/TFA (95/5/0.1) |
| Column | Waters X-Bridge phenyl, 3.5 µm, 150 × 4.6 mm |
| Column temperature | 30° C. |
| Autosampler temperature | Ambient |

TABLE 2-continued

| Impurities determination parameters | | | |
|---|---|---|---|
| Flow rate | 1.0 mL/min | | |
| Injection volume | 10 µL | | |
| Detection | UV@ 254 nm | | |
| Gradient | Time | % A | % B |
| | 0 | 100 | 0 |
| | 2 | 100 | 0 |
| | 15 | 0 | 100 |
| | 25 | 0 | 100 |
| | 27 | 100 | 0 |
| | 37 | 100 | 0 |
| Diluent | Acetonitrile:water (50:50) | | |
| Sample concentration | 0.2 mg/mL | | |
| Standard concentration | 2 µg/mL | | |

Products Tested

The effect of different sterilisation techniques were assessed on:
(i) suspension formulations comprising ensifentrine particles (terminal sterilisation); and
(ii) ensifentrine particles prior to formulation as a suspension (aseptic compounding and filling).

Three aqueous suspensions having the formulations shown in Tables 3 to 5 were prepared.

TABLE 3

| Variant 1a (0.4 mg/ml, pH 6.7) | |
|---|---|
| Constituent | Concentration (mg/ml) |
| Micronised ensifentrine | 0.4 |
| Polysorbate 20 | 0.5 |
| Span 20 (sorbitan monolaureate) | 0.05 |
| Monosodium phosphate anhydrous | 5.72 |
| Dibasic sodium phosphate anhydrous | 6.80 |
| Sodium chloride | 4.80 |
| Water | N/A |

TABLE 4

| Variant 2a (0.4 mg/ml, pH 5.9) | |
|---|---|
| Constituent | Concentration (mg/ml) |
| Micronised ensifentrine | 0.4 |
| Polysorbate 80 | 0.5 |
| Citric acid monohydrate | 1.68 |
| Trisodium citrate dihydrate | 27.06 |
| Sodium chloride | 9.0 |
| Water | N/A |

TABLE 5

| Variant 3a (0.4 mg/mL, pH 7.1) | |
|---|---|
| Constituent | Concentration (mg/ml) |
| Micronised ensifentrine | 0.4 |
| Polysorbate 20 | 0.5 |
| Sodium chloride | 9.0 |
| NaOH | N/A |
| Water | N/A |

The unformulated ensifentrine particles were assessed as a dry powder.

Sterilisation Techniques

The sterilisation techniques shown in Table 6 were assessed.

TABLE 6 sterilisation techniques

| Technique | Method |
| --- | --- |
| A | Terminal sterilisation of the aqueous suspension formulations by heat treatment: each of variants 1a, 2a and 3a of the suspension formulation were heat treated in an autoclave at 121° C. for 15 minutes. |
| B | Terminal sterilisation of the aqueous suspension formulations by gamma irradiation: each of variants 1a, 2a and 3a of the suspension formulation were gamma irradiated at 25kGy-30kGy. |
| C | Dry heat sterilisation of micronised ensifentrine: a dry powder of the micronised ensifentrine was heat treated in an open glass vial in an oven at 150° C. for 150 minutes. |
| D | Dry heat sterilisation of micronised ensifentrine: a dry powder of the micronised ensifentrine was heat treated in an open glass vial in an oven at 160° C. for 120 minutes. |
| E | Dry heat sterilisation of micronised ensifentrine: a dry powder of the micronised ensifentrine was heat treated in an open glass vial in an oven at 170° C. for 60 minutes. |
| F | Dry gamma irradiation of micronised ensifentrine: a dry powder of the micronised ensifentrine was gamma irradiated at 25kGy-30kGy. |

The sterilised micronised ensifentrine obtained from techniques C to F may be subsequently combined with an aseptic vehicle to obtain a suspension formulation.

Results

The assays and related substances of the products obtained by each of sterilisation techniques A to F were assessed by the HPLC methods described above. The results are summarised in Table 7.

TABLE 7 assessment of products

| Technique | Assessment |
| --- | --- |
| A: terminal heat treatment | No change in appearance of the suspension formulations was observed. Significant impurities were however observed for variants 1a and 2a (RTT 0.79, 2.5% nominal) and variant 3a (RRT 0.87, 5.8% nominal). The assay results were correspondingly lower compared to untreated samples, with variant 1a dropping by 5%, variant 2a by 2.5% and variant 3a by approximately 8%. |
| B: terminal gamma irradiation | Upon irradiation, a brown discolouration of the glass was apparent. Variant 3a was found to have converted to a pale yellow solution. The related substances analysis showed clear degradation to a large number of impurities totalling nearly 7% nominal for variant 2a and 2.6% nominal for variant 3a. Variant 1a showed no change in total related substances when compared to the untreated sample, but there was a drop in assay suggesting product loss or degradation that was not visible in the chromatogram. A large drop in assay was observed for all variants. |
| C: dry heat treatment (150° C. for 150 minutes) | No significant changes observed. |
| D: dry heat treatment (160° C. for 120 minutes) | No significant changes observed. |
| E: dry heat treatment: (170° C. for 60 minutes) | No significant changes observed. |
| F: dry gamma irradiation | An increase in total impurities of 0.5% w/w was observed with a decrease in assay of around 1 to 1.5% w/w. |

CONCLUSION

The results in Table 7 indicated that terminal heat treatment (technique A), terminal gamma irradiation (technique B) and dry gamma irradiation (technique F) caused some degradation when used for preparation of a sterilised suspension of ensifentrine particles.

It was found, however, that ensifentrine particles were highly resistant to sterilisation by dry heat treatment, with no significant changes in purity or assay following treatment at temperatures of from 150° C. to 170° C. Dry heat treatment at 160° C. for at least 120 minutes is preferred. The sterilised ensifentrine particles obtained by dry heat treatment can be combined with the suspension vehicle in aseptic compounding and processing to obtain a sterile suspension formulation comprising ensifentrine.

What is claimed is:

1. A method for producing a sterile liquid pharmaceutical composition comprising sterile ensifentrine particles suitable for administration by inhalation, the method comprising:
    (a) heating ensifentrine particles at a temperature of from 100° C. to 220° C. to obtain the sterile ensifentrine particles, wherein the heating produces less than a 0.5% w/w increase in total impurities; and
    (b) combining the sterile ensifentrine particles with a sterile liquid vehicle to produce the sterile liquid pharmaceutical composition suitable for administration by inhalation.

2. The method of claim 1, wherein the method comprises heating the ensifentrine particles at a temperature of from 120° C. to 200° C.

3. The method of claim 2, wherein the method comprises heating the ensifentrine particles at a temperature of from 140° C. to 180° C.

4. The method of claim 1, wherein the method comprises heating the ensifentrine particles for from 10 minutes to 24 hours.

5. The method of claim 4, wherein the method comprises heating the ensifentrine particles for from 30 minutes to 360 minutes.

6. The method of claim 1, wherein the method comprises heating the ensifentrine particles at a temperature of from 145° C. to 175° C. for from 45 minutes to 160 minutes.

7. The method of claim 6, wherein the method comprises heating the ensifentrine particles at a temperature of from 155° C. to 165° C. for from 110 minutes to 130 minutes.

8. The method of claim 1, wherein the sterile ensifentrine particles comprise at least 95% by weight of ensifentrine or a pharmaceutically acceptable salt thereof relative to a total weight of the sterile ensifentrine particles.

9. The method of claim 1, wherein the sterile ensifentrine particles comprise at least 95% by weight of ensifentrine free base relative to a total weight of the sterile ensifentrine particles.

10. The method of claim 1, wherein the ensifentrine particles are in a form of a dry powder.

11. The method of claim 1, wherein the sterile ensifentrine particles have a particle size distribution with a Dv10 of from 0.1 μm to 1.0 μm.

12. The method of claim 1, wherein the sterile ensifentrine particles have a particle size distribution with a Dv50 of from 0.5 μm to 5.0 μm.

13. The method of claim 1, wherein the sterile ensifentrine particles have a particle size distribution with a Dv90 of from 2.5 μm to 6 μm.

14. The method of claim 1, wherein the method further comprises subjecting a liquid vehicle to aseptic filtration to produce the sterile liquid vehicle.

15. The method of claim 1, wherein the sterile liquid vehicle comprises a diluent and optionally one or more additional excipients selected from surfactants, buffers, and tonicity adjusters.

16. The method of claim 15, wherein the sterile liquid pharmaceutical composition comprises:
    (a) sterile ensifentrine particles at a concentration of from 0.5 mg/mL to 6 mg/mL;
    (b) one or more surfactants at a concentration of from 0.01 mg/mL to 2 mg/mL;
    (c) a buffer at a concentration of from 0.6 mg/mL to 4 mg/mL;
    (d) a tonicity adjuster at a concentration of from 5 mg/mL to 12 mg/mL.

17. The method of claim 16, wherein the sterile liquid vehicle comprises water, sodium chloride, sodium dihydrogen phosphate dihydrate, disodium hydrogen phosphate dihydrate, polysorbate 20, or sorbitan laurate.

18. The method of claim 17, wherein the sterile liquid pharmaceutical composition comprises:
    (a) sterile ensifentrine particles at a concentration of from 0.5 mg/mL to 6 mg/mL;
    (b) polysorbate 20 at a concentration of from 0.1 mg/mL to 1.5 mg/mL;
    (c) sorbitan monolaurate at a concentration of from 0.01 mg/mL to 0.5 mg/mL;
    (d) sodium dihydrogen phosphate dihydrate at a concentration of from 0.3 mg/mL to 2 mg/mL;
    (e) disodium hydrogen phosphate dihydrate at a concentration of from 0.3 mg/mL to 2 mg/mL; and
    (f) sodium chloride at a concentration of from 5 mg/mL to 12 mg/mL,
    wherein a total weight of ensifentrine in the sterile liquid pharmaceutical composition is from 2.7 to 3.3 mg.

19. The method of claim 1, wherein the sterile liquid pharmaceutical composition comprises sterile ensifentrine particles at a concentration of from 0.1 mg/mL to 5 mg/mL.

20. The method of claim 18, wherein the sterile liquid pharmaceutical composition comprises sterile ensifentrine particles at a concentration of from 1 mg/mL to 2 mg/mL.

21. The method of claim 1, wherein a pH of the sterile liquid pharmaceutical composition is from 6 to 7.5.

22. The method of claim 21, wherein the pH of the sterile liquid pharmaceutical composition is from 6.2 to 7.2.

23. The method of claim 1, wherein the sterile ensifentrine particles are re-suspendable in the sterile liquid vehicle.

24. The method of claim 1, wherein the method does not comprise heating the sterile liquid pharmaceutical composition at a temperature of 100° C. or greater.

25. The method of claim 1, wherein the sterile liquid pharmaceutical composition is suitable for use in a nebulizer.

* * * * *